United States Patent [19]
Haas et al.

[11] Patent Number: 5,517,861
[45] Date of Patent: May 21, 1996

[54] HIGH TEMPERATURE CRACK MONITORING APPARATUS

[75] Inventors: Robert J. Haas, Coventry; Michael Winter, New Haven; Balkrishna S. Annigeri, Manchester; Leroy H. Favrow, Newington, all of Conn.; Jason S. Wegge, Springfield, Mass.

[73] Assignee: United Technologies Corporation, Hartford, Conn.

[21] Appl. No.: 320,817

[22] Filed: Oct. 11, 1994

[51] Int. Cl.$^6$ .................................................. G01N 3/08
[52] U.S. Cl. .................................. 73/799; 73/800; 356/237
[58] Field of Search ............................ 73/799, 800, 786, 73/788, 790, 796, 806, 807, 808, 813, 816, 821, 830, 834; 356/237

[56] References Cited

U.S. PATENT DOCUMENTS

| | | | |
|---|---|---|---|
| 4,175,447 | 11/1979 | FuKuhara | 73/799 |
| 4,233,849 | 11/1980 | Defebvre et al. | 73/812 |
| 4,307,610 | 12/1981 | Leupp | 73/799 |
| 4,394,683 | 7/1983 | Liptay-Wagner et al. | 358/107 |
| 4,572,663 | 2/1986 | Greene et al. | 356/23 |
| 4,574,642 | 5/1986 | Fleischman | 73/799 |
| 4,591,996 | 5/1986 | Vachon | 73/800 |
| 4,636,638 | 1/1987 | Huang et al. | 73/800 |
| 4,653,109 | 3/1987 | Lemelson et al. | 382/34 |
| 4,716,459 | 12/1987 | Makabe et al. | 73/799 |
| 4,836,031 | 6/1989 | Jatho et al. | 73/800 |
| 4,869,110 | 9/1989 | Kent et al. | 73/800 |
| 4,875,170 | 10/1989 | Sakurai et al. | 364/507 |
| 4,953,973 | 9/1990 | Leftheris et al. | 73/800 |
| 4,972,073 | 11/1990 | Lessing | 73/800 |
| 5,394,752 | 3/1995 | Reda | 73/800 |

OTHER PUBLICATIONS

System Description and Operating Instructions for Model PN–232 entitled "Laser–Augmented Welding Vision System" manufactured by Control Vision, Inc.
Documentation entitled "Some Benefits of Laser–Enhanced Welding Vision" by Control Vision, Inc.
Documentation entitled "Laser Video for Welding . . . Arc Welding Without the Arc!" by Control Vision, Inc.
Paper entitled "Measurement of Small Cracks by Photomicroscopy: Experiments and Analysis" by James M. Larsen et al.
ASTM Special Technical Publication 1149, pp. 92–115, W. N. Sharpe, Jr. et al., "Real–Time Measurement of Small-Crack Opening Behavior Using an Interferometric Strain/Displacement Gage".

Primary Examiner—Richard Chilcot
Assistant Examiner—Eric S. McCall
Attorney, Agent, or Firm—Pamela J. Curbelo

[57] ABSTRACT

An apparatus for monitoring the growth of surface cracks in materials includes a servo-hydraulic test machine which applies a load to a specimen according to a predetermined loading regime designed to induce crack growth in the specimen, a UV laser for illuminating the specimen with a light having a frequency greater than the frequency of incandescent light, a UV video camera and a two dimensional imaging computer. Optionally, the two dimensional imaging computer can be used to control the servo-hydraulic test machine.

23 Claims, 3 Drawing Sheets $t_0$ $t_1$ $t_2$ $t_1-t_0$ $t_2-t_1$ $t_1-t_0$ $t_2-t_1$ $t_1-t_0$ $t_2-t_1$

HIGH TEMPERATURE CRACK MONITORING APPARATUS

Technical Field

This invention relates to an apparatus for monitoring crack growth in materials while under a load, and especially for monitoring crack growth in an incandescent specimen while under a load.

Background Information

In material and product development, an understanding of material behavior prior to integration into a final product is important for both safety and economic reasons. Anticipation of how a material will perform in a product under service conditions requires characterization of the materials' mechanical properties. For example, materials under a prolonged cyclic loading can undergo catastrophic failure due to initiation of cracks and their rapid growth. Consequently, emphasis has been placed on understanding the behavior of materials during cyclic loading, and particularly during cyclic loading of a heated specimen where the loading simulates how that material will actually be used.

Most conventional apparatus, however, cannot measure crack formation and propagation during cyclic loading of a material. Therefore, testing of a material during a typical cyclic loading regime creates many problems. For example, monitoring surface crack formation and propagation comprises capturing an image and measuring the crack's dimensions from that image. Since the movement of the specimen during cyclic loading does not allow for clear photographic images, the loading regime must be stopped, periodically, for photographic work. This is very time consuming and it allows the material to relax outside of the intended loading regime which can lead to anomalous results.

Another method of monitoring crack growth which has problems similar to the still photography comprises surface replication coupled with the use of a Transmission Electron Microscope (TEM). Here the loading regime is periodically stopped to make an acetate replicate of a surface of the specimen. The replicate is viewed under a TEM to observe crack formation and growth. This method not only comprises an undesirable relaxation period, it is very time consuming and expensive.

In addition to long down times, high cost, and alterations of the anticipated loading regime, the analysis of crack growth typically proceeds by manual calculations requiring physical measurements of photographs. The measurements are performed by placing a reference mark of predetermined length on the specimen prior to testing such that crack lengths can be measured with respect to the reference mark. The changes in crack size can be calculated directly from the measurements of the crack, or the total crack size can be determined by comparing the length of the crack to the reference mark. Since this technique includes several points of human intervention, there is a potential for error. This limitation of the monitoring apparatus can lead to an increased error in the characterization of a material, high cost, and long test periods.

Another drawback of conventional apparatus is a lack of automatic shut off based upon crack size. Because a specimen can undergo thousands of load cycles during a single test, the actual point of crack initiation is often not recorded and the specimen is cycled until failure. Consequently, some of the early stage characteristics of a surface crack are destroyed, rendering that test data less valuable since the shape and pattern of a crack initiation and growth are needed for subsequent crack growth modeling.

Furthermore, when monitoring a material for thermal mechanical fatigue, current technology relies upon an electrical potential drop technique to detect and monitor crack initiation and growth. This technique comprises passing an electrical current through a heated specimen and monitoring the change in the electrical resistance through the specimen to determine the initiation and growth of a crack. The data is then calibrated to determine the crack shape and size. As is evident from the above description, this technique is time consuming and inherently has a large potential for inaccurate data.

Therefore, what is needed in the industry is an apparatus capable of accurately measuring crack growth of a hot specimen, real time.

SUMMARY OF THE INVENTION

The present invention relates to a method and apparatus for monitoring cracks in a specimen. The apparatus of the present invention comprises: means for applying a load to the specimen, means for illuminating the specimen during the application of a load with a light having a frequency which is both higher than the frequency of incandescent light and greater or equal to the frequency of the means for applying a load, means for capturing reflected illuminating light from the specimen, wherein said light capturing means captures reflected illuminating light to form an image of the specimen and wherein said light capturing means is phase synchronized with said illuminating means such that crack formation images can be obtained during the application of a load, and means for processing images obtained by said light capturing means.

The method of the present invention comprises: applying a load to the specimen, illuminating the specimen with a light during the application of the load to accentuate the formation of cracks, wherein said light has a frequency greater than incandescent light frequency, capturing reflected illuminating light from the specimen and forming a image of the specimen from the reflected light, and processing the images.

BEST MODE FOR CARRYING OUT THE INVENTION

Real time monitoring of crack formation and growth in a hot specimen is difficult due to the fact that the specimen becomes incandescent at high temperatures, thereby masking any cracks and rendering them seemingly invisible. This masking effect occurs at different temperatures for different materials as is readily determined by an artisan, i.e. metals typically become incandescent at temperatures exceeding about 1500° F. while ceramics typically become incandescent at temperatures exceeding about 1100° F. It has been discovered, however, that if an incandescent specimen is illuminated with a light having a frequency greater than the frequency of the incandescent light, an image can be formed by the reflected higher frequency light. For example, an ultraviolet (UV) laser can be employed to illuminate an incandescent specimen and the reflected UV light can be captured to form a crack revealing image of the specimen.

Figure 1:
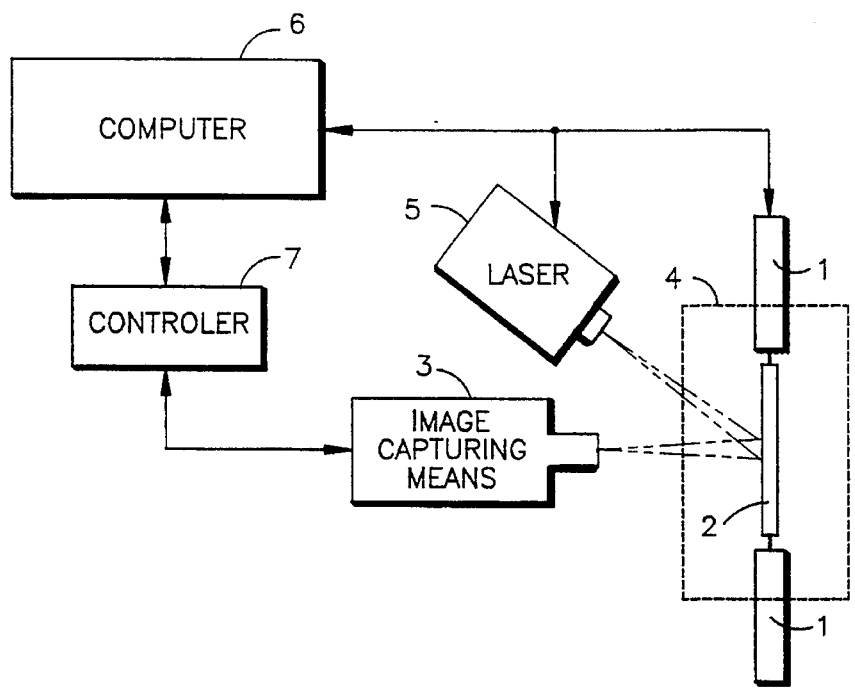
FIG. 1 is an overall schematic of the invention.

Consequently, referring to FIG. 1, one embodiment of the apparatus of the present invention includes: means for heating the specimen 4 such as an oven, furnace, heating coils, or other conventional heating means, means for applying a load 1 to a specimen 2 to simulate actual use, means for illuminating 5 the specimen with UV light to accentuate the formation of cracks on the surface of the specimen, means for capturing reflected UV light 3 to form images of the specimen 2 at predetermined points in the loading regime, and means for processing the images 6 to monitor the changes in a crack's dimensions during the loading regime. Optionally, a means for controlling 7 the loading means 1, illuminating means 5, and the UV light capture means 3 can be attached to the processing means 6 to implement the results obtained from the processing means 6 in controlling the operation of the other means. For example, the load or cycle rate can be increased or decreased, the loading can be terminated when the crack reaches a predetermined length, and the illumination means 5 and UV light capture means 3 can be moved to obtain better light contrast.

The means for applying a load 1 to a specimen 2 can be any conventional device that can impart a loading regime to a specimen, with a means which can closely simulate the loading regime of an actual component formed from the material of the specimen, generally preferred. These machines include, but are not limited to, servo-hydraulic and electric test machines, such as a 3310 series, 100 kN capacity, universal testing machine produced by Interlaken Technology Corporation (Minnesota, USA). Similar machines are produced by Instrom Corporation, Canton, Mass., and MTS System Corporation, Minneapolis, Minn., among others.

While the loading means 1 applies a load to the specimen 2, the illuminating means 5 illuminates the specimen 2 to allow monitoring of crack formation and growth. Since monitoring typically occurs at a microscopic level, surface preparation of the specimen can be very important in order to obtain the desired illumination and contrast of any cracks which form. Typically, conventional surface preparation techniques can be used either alone or combinations thereof, such as the ASTM preparation standards. The specimen should be prepared to obtain preferential etching of the such that grain boundaries and other microstructural features will not be highlighted to the point that these boundaries and features can not be distinguished from cracks.

The illuminating means 5 may be any conventional lighting device that illuminates the specimen with a light which is sufficiently reflected by the specimen such that the reflected light can be captured to form an image of the specimen and having an optical frequency which is higher than the optical frequency of the incandescent light emitted by the specimen and a pulse frequency greater than or equal to the test frequency of the loading means 1. Additionally, this illuminating means 5 preferably provides considerable flexibility in illuminating the area of the specimen where cracks occur. Generally, any conventional UV laser can be employed, such as a pulsed nitrogen UV laser having a wavelength of 337 nanometers, produced by Photo Chemical Research Associates, London, Ontario, Canada, or by Laser Science, Inc., Newton, Mass. Due to the concentrated nature of the light from the laser, i.e. the light only illuminates a small area of the specimen, the light is preferably diffused to both light a larger area of the specimen and to allow the reflected light capturing means to form a clear image. If the light is too concentrated many conventional image capturing means can not handle the light and will fail. Any conventional diffusion means can be used, with ground glass preferred.

The orientation of the illuminating means 5 is important due to the desire to obtain maximum image contrast for observing the crack and thereby enhance the accuracy of the crack monitoring. Typically the illuminating means 5's location, with respect to the surface of the specimen 2, is dictated either by the presence of a surface notch which sets up a crack formation site or by the geometry of the specimen. Note, surface feature contrast is particularly important when monitoring shallow cracks which do not usually provide sufficient contrast in lighting and shadowing to enable accurate crack monitoring.

Additionally, in order to allow proper comparison of images and therefore proper crack growth monitoring, it is preferred that the illuminating means 5 illuminate the specimen 2 for as short a time as possible. Short illumination times enable the capture of images only at a predetermined point or phase in the loading regime, thereby reducing or eliminating image blur due to subject motion and enhancing image accuracy. Times on the order of a few nanoseconds up to about 10 microseconds ($\mu$sec) can be used, with less than about 5 $\mu$sec preferred, and less than about 1.5 $\mu$sec especially preferred. The time may be determined by the specimen's velocity which is a function of the magnitude and variation of the load and composition of the specimen 2, with consideration given to the magnification used by the imaging means 3.

To further reduce or eliminate image blur and to ensure image capture at a desired point in the loading regime, the loading means 1 and the illumination means 5 can be phase synchronized so that illumination only occurs at the desired points in the loading. For example, the loading means 1 and illumination means 5 can be phase synchronized or phased so that illumination and image capture both occur when the load is at the point of maximum crack opening.

After the illuminating means 5 illuminates the specimen 2 with UV light, the UV light is reflected off the specimen 2 and captured by means for capturing reflected UV light 3 which is preferably phase synchronized with both the application of a load to the specimen 2 and the illumination. This UV light capturing means 3 is typically any conventional imaging device capable of sufficiently sensing the reflected UV light to form an image of the specimen 2 such that crack formation and growth data can be obtained, monitored, and preferably magnified. Typically a UV video camera is employed, such as an intensified video camera; i.e. the 4 Quick 05 camera by Stanford Computer Optics, Inc., Palo Alto, Calif.. The desired resolution capabilities of the camera, which can readily be determined by an artisan, are typically up to about 20 microns ($\mu$) (about 0.78 mils). In one application, for example, an intensified UV video camera having an about 2 micron resolution capability was used to monitor a specimen where crack formation was estimated to occur based on the geometry of the specimen.

In order to improve the resolution of the captured image, the UV light capturing means 3 can include a magnification means. This magnification means can be any conventional device capable of either magnifying the image prior to the sensing of the UV light by the light capturing means 3 or of magnifying the captured image. Possible devices include, but are not limited to, microscopes, macrophoto lenses, and electronic image magnification devices. Due to the heating of the specimen and the use of UV light, microscopes or other magnifying means comprising quartz optics are preferred, such as the Questar microscope produced by Questar Corporation, New Hope, Pa., having a working distance of about 6 to about 14 inches, quartz optics, and 2 µ resolution. The cameras and microscopes can be mounted on a device, such as a tripod or other support device, i.e. x, y, z stage, which enables focusing on any desired point on the specimen.

Also employed to allow real time monitoring of crack formation and growth is a processing means 6 which connects to and utilizes the image from the UV light capturing means 3. This processing means 6 can be any conventional device capable of real time processing of the data from the UV light capturing means 3, such as a device capable of digital processing the data from the UV light capture means 3 to automatically extract crack growth data. One such device is a two dimensional imaging computer system capable of quantitatively analyzing recorded crack growth data using software that real time image processes that data. This software, which can be any software capable of processing the crack growth data, preferably provides real time zoom and enhancement capabilities and effectuates two dimensional imaging. For example, OMA software developed by M. Long at Yale University (New Haven, Conn., USA) can be used for quantitative analysis and image processing, while IMAGE software developed by the National Institutes of Health (Bethesda, Md., USA) can be used for real time monitoring of the image capturing means signals and for providing real time zoom and enhancement capabilities for crack detection.

Figure 2:
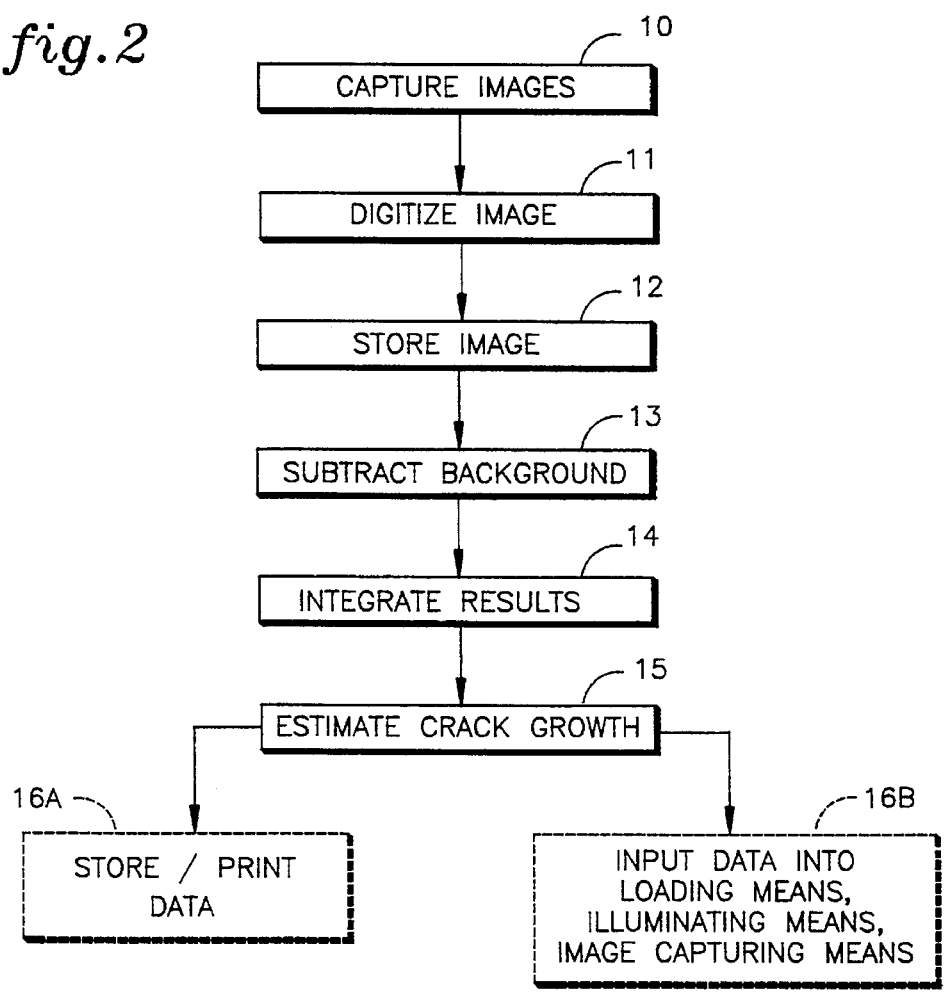
FIG. 2 is a block diagram of the processing means used to monitor the changes in a crack's dimension.

FIG. 2 illustrates the flow of data through the processing means 6. This set up enables digitization of the images allowing the computer to subtract out background images and concentrate on changes in a crack's dimensions. An image is formed from captured reflected UV light 10, the image is computer digitized 11, and then stored 12. The computer subtracts a previously digitized image (the background) 13 from the new image, records the difference in the two images, and integrates across the crack 14 to show the change in the crack's size and location along a single vector axis. This data can then be analyzed accordingly. For example, mean crack growth 15 can be determined by comparing the center point of the location and size of the crack along a single vector axis, the "centroid", of the portion of the crack that is left after the background has been subtracted away, the "crack tips".

Figure 3A:
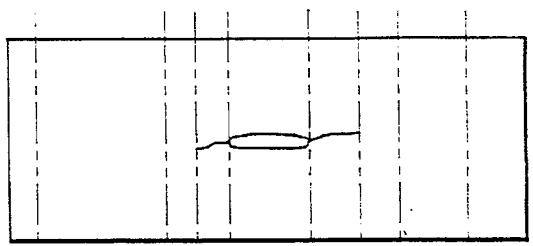
FIGS. 3A–3C show images of cracks at different points in time in the loading regime.
Figure 3B:
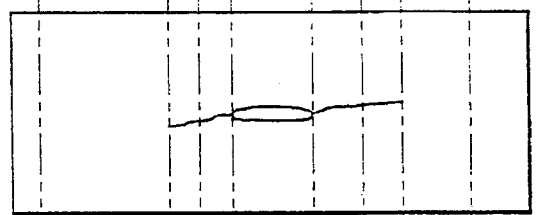
Figure 3C:
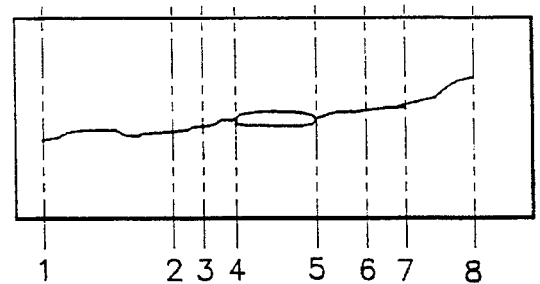
Figure 4A:
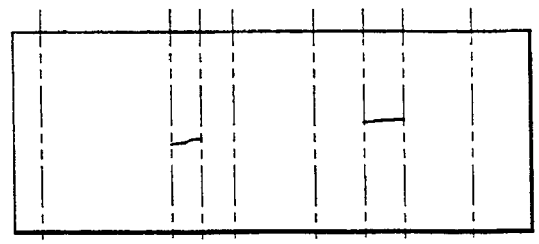
FIGS. 4A–4B show the changes in a crack's dimensions after subtracting out a previous image.
Figure 4B:
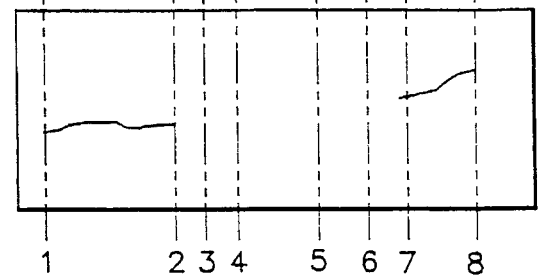
Figure 5A:
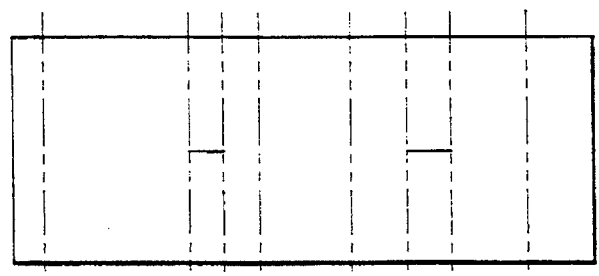
FIGS. 5A–5B show the integration of the changes in the crack into a single vector axis.
Figure 5B:
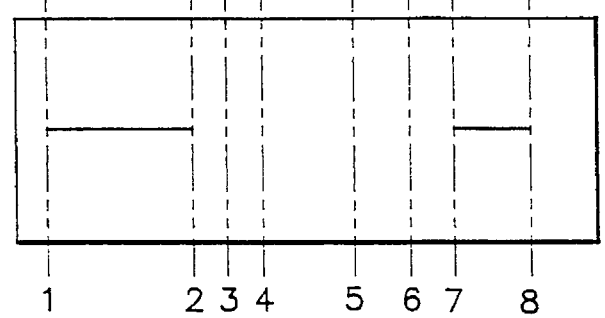
Figure 6A:
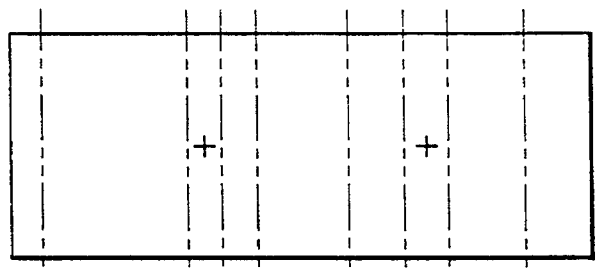
FIGS. 6A–6B show the location of the centroid of the crack tips.
Figure 6B:
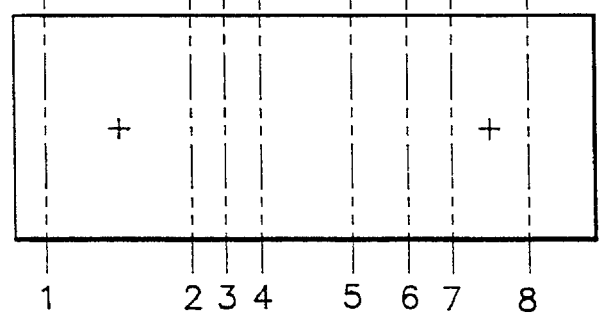

FIGS. 3A–6B illustrate the operations of the processing means 6. FIGS. 3A–3C show a crack image at three different times during a loading regime. FIGS. 4A–4B illustrate the subtraction of an image from the background. In FIGS. 5A–5B the subtracted images are integrated to be represented on one axis. In FIGS. 6A–6B, the centroid of the crack (represented at this point as a single direction vector) is located so the computer can estimate the crack growth. The mean crack growth data can then be printed and/or stored 16A (see FIG. 2), recording the entire crack formation, or if desired, only the changes in the specimen's surface topography.

Since automated phase synchronization of the loading means 1, the illuminating means 5, and the UV light capturing means 3 will improve the capture of images at a predetermined point in the loading, a controlling means 7 can optimally be attached to the processing means 6 to control the other means (see 16B of FIG. 2). The controlling means 7 can use data obtained from the processing means 6 to alter the load during deformation at the site of a crack or to stop the loading when a crack reaches a predetermined size, and to locate a site of crack formation on a specimen surface and move the UV light capturing means 3 and illuminating means 5 to focus upon that site. Ultimately, the controlling means 7 can be used to automatically operate the entire or any part of the apparatus by using data from an operator and/or output from the processing means 6.

Although the invention has been described and illustrated with respect to the exemplary embodiments thereof, it should be understood by those skilled in the art that the foregoing and various other changes, omissions and additions may be made without departing from the spirit and scope of the invention.

We claim:

1. An apparatus for monitoring cracks in a specimen which emits incandescent light, comprising:
   a. means for applying a load to the specimen, wherein said means for applying a load has a test frequency;
   b. means for illuminating the specimen during the application of a lead with a light having an optical frequency which is higher than the optical frequency of incandescent light and a pulse frequency greater than or equal to said test frequency of said means for applying a load, wherein said light is transmitted light;
   c. means for capturing reflected, transmitted light from the specimen, wherein said light capturing means captures reflected illuminating light to form an image of the specimen and wherein said light capturing means is phase synchronized with said illuminating means such that crack formation images can be obtained during the application of a load; and
   d. means for processing images obtained by said light capturing means.

2. The apparatus of claim 1, wherein said means for applying a load is capable of applying a loading regime to the specimen which simulates the loading regime of an actual component.

3. The apparatus of claim 1, wherein the means for illuminating the specimen and the specimen are arranged to provide as much image contrast as possible.

4. The apparatus of claim 1, wherein said means for illuminating and said means for applying a load each have a frequency and wherein said frequencies are phase synchronized.

5. The apparatus of claim 1, wherein the means for processing includes means for digitizing a first captured image, storing that image, then subtracting out the first captured image from a second captured-digitized image, integrating the subtracted images, and estimating crack growth.

6. The apparatus of claim 1, further comprising a means for storing and printing crack growth data.

7. The apparatus of claim 1, further comprising a means for controlling wherein said means for controlling controls said means for applying a load, said illuminating means, and said UV light capturing means by using data from said processing means or data input by an operator.

8. The apparatus of claim 1, further comprising a means for heating the specimen.

9. The apparatus of claim 1, wherein said light capturing means further comprises a magnification means.

10. The apparatus of claim 1, further comprising a diffusion means for diffusing the illuminating light.

11. The apparatus of claim 10, wherein said diffusion means is ground glass.

12. A method for monitoring crack growth in a specimen which emits incandescent light, comprising the steps of:
   a. applying a load to the specimen using a means for applying a load, wherein the means for applying a load has a test frequency;
   b. illuminating the specimen with a light during the application of the load, to accentuate crack formation, wherein said light has an optical frequency which is greater than incandescent light optical frequency and a pulse frequency greater than or equal to the test frequency of the means for applying a load, wherein said light is transmitted light;
   c. producing crack growth data by capturing reflected, transmitted light from the specimen and forming a image of the specimen from the reflected light; and
   d. processing the crack growth data.

13. The method of claim 12, further comprising heating the specimen prior to illuminating the specimen.

14. The method of claim 12, wherein the load is applied to the specimen to simulate a loading regime of an intended use of the specimen.

15. The method of claim 12, wherein the specimen is oriented to provide as much light contrast as possible during illumination.

16. The method of claim 12, wherein said illumination and said application of a load occur at phase synchronized frequencies.

17. The method of claim 12, wherein said illumination and said UV light capturing occurs at a like point in the loading regime.

18. The method of claim 12, wherein said illumination and said image capturing occur at a point in the loading regime where a crack having a maximum dimension is opened to said maximum dimension.

19. The method of claim 12, wherein said processing includes digitizing a first captured image, storing that image, subtracting out the first captured image from a second captured-digitized image, integrating the subtracted images, and estimating crack growth.

20. The method of claim 12, further comprising storing and printing the crack growth data.

21. The method of claim 12, further comprising controlling said loading, said illuminating, and said UV light capturing using crack growth data or data input by an operator.

22. The method of claim 12, further comprising magnifying the reflected light to improve the image.

23. The method of claim 12, further comprising diffusing the illuminating light.

* * * * *

UNITED STATES PATENT AND TRADEMARK OFFICE
CERTIFICATE OF CORRECTION

PATENT NO.  : 5,517,861
DATED       : May 21, 1996
INVENTOR(S) : Robert J. Haas et al.

It is certified that error appears in the above-indentified patent and that said Letters Patent is hereby corrected as shown below:

Claim 1, Column 6, line 26, "lead" should read --load--.
Claim 7, Column 6, line 62, delete "UV".

Signed and Sealed this

Twenty-third Day of November, 1999

Attest:

Q. TODD DICKINSON

*Attesting Officer*      *Acting Commissioner of Patents and Trademarks*